United States Patent

Jensen et al.

[11] Patent Number: 6,143,798
[45] Date of Patent: *Nov. 7, 2000

[54] WOUND DRESSING

[75] Inventors: Jarl B. Jensen, River Vale; Anil Torjalkar, Cranbury, both of N.J.

[73] Assignee: Jentec, Inc., Northvale, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/228,335

[22] Filed: Jan. 11, 1999

[51] Int. Cl.⁷ .......................... A61K 47/30; C08G 63/48
[52] U.S. Cl. .......................... 514/772.1; 525/63
[58] Field of Search .................. 524/22; 428/231; 128/155; 424/445, 443; 525/63; 514/772.1, 72.6, 788.1

[56] References Cited

U.S. PATENT DOCUMENTS

| | | |
|---|---|---|
| 3,339,546 | 9/1967 | Chen . |
| 3,532,679 | 10/1970 | Steckler . |
| 3,888,247 | 6/1975 | Stenvall ................. 128/155 |
| 3,980,084 | 9/1976 | Kross . |
| 4,166,051 | 8/1979 | Cilento et al. . |
| 4,192,785 | 3/1980 | Chen et al. . |
| 4,204,540 | 5/1980 | Cilento et al. . |
| 4,231,369 | 11/1980 | Sorensen et al. . |
| 4,367,732 | 1/1983 | Poulsen et al. . |
| 4,369,284 | 1/1983 | Chen . |
| 4,477,325 | 10/1984 | Osburn . |
| 4,496,357 | 1/1985 | Osburn . |
| 4,538,603 | 9/1985 | Pawelchak et al. . |
| 4,551,490 | 11/1985 | Doyle et al. . |
| 4,768,503 | 9/1988 | Highgate et al. . |
| 4,867,748 | 9/1989 | Samuelsen . |
| 4,952,618 | 8/1990 | Olsen . |
| 5,006,401 | 4/1991 | Frank ...................................... 428/231 |
| 5,133,821 | 7/1992 | Jensen . |
| 5,508,334 | 4/1996 | Chen . |
| 5,571,080 | 11/1996 | Jensen . |
| 5,622,711 | 4/1997 | Chen . |
| 5,633,010 | 5/1997 | Chen . |
| 5,704,905 | 1/1998 | Jensen et al. . |
| 5,733,570 | 3/1998 | Chen et al. . |
| 5,762,620 | 6/1998 | Cartmell et al. . |
| 5,827,528 | 10/1998 | Kubo et al. ............................. 424/443 |

FOREIGN PATENT DOCUMENTS 788784  8/1997  European Pat. Off. ........ A61F 13/02

*Primary Examiner*—William R. A. Jarvis
*Assistant Examiner*—Vickie Kim
*Attorney, Agent, or Firm*—McDonnell Boehnen Hulbert & Berghoff

[57] ABSTRACT

The invention provides compositions suitable for use as a wound dressings for blisters, corns and calluses or as fixation adhesives, especially for breast prostheses, ostomy devices and male incontinence devices, and the like. In preferred embodiments, the composition comprises an elastomer, optionally a hydrocolloid, a hydrocarbon resin tackifier, a non-polar oily extender and no more than about 0.1 weight percent of an antioxidant.

19 Claims, No Drawings though the composition of blisters on the foot, as well as corns and calluses. The embodiments of the invention are also suitable for use as fixation adhesives, especially for breast prostheses, ostomy devices and male incontinence devices, and the like. Notable features of the composition include translucent clarity, minimal antioxidant content, and the use of a non-polar oily extender, preferably mineral oil, that is substantially non-irritating to the skin.

WOUND DRESSING

BACKGROUND OF THE INVENTION

The present invention provides an elastomer based adhesive composition that is conformable and flexible. The composition is suitable for use as a dressing for the treatment of wounds. The advantages provided by the composition produce a wound dressing that is particularly suitable for the treatment of blisters, especially blisters on the foot, as well as corns and calluses. The embodiments of the invention are also suitable for use as fixation adhesives, especially for breast prostheses, ostomy devices and male incontinence devices, and the like. Notable features of the composition include translucent clarity, minimal antioxidant content, and the use of a non-polar oily extender, preferably mineral oil, that is substantially non-irritating to the skin.

Hydrocolloid adhesive compositions, as well as wound dressings and ostomy products formed from these adhesive compositions, have been known for many years. Typically, these compositions comprise a blend of a polymer matrix, such as a rubbery elastomer like polyisobutylene, in combination with one or more water-soluble or water-swellable hydrocolloids, such as a dry powdered mixture of pectin, gelatin and carboxymethylcellulose. When included in a wound dressing or ostomy seal, the adhesive composition is usually coated on at least one surface of a water-insoluble film. See e.g., U.S. Pat. Nos. 3,980,084, 3,877,431, 3,532,679, and 3,339,546.

A major problem with many conventional hydrocolloid adhesive compositions is their susceptibility to breakdown upon exposure to wound exudate and body fluids (i.e. their lack of structural integrity after being hydrated). Another problem with many conventional hydrocolloid adhesive compositions is their initial lack of tack at room temperature. In many cases, the applied dressing must be warmed for several minutes by placing a hand tightly over the dressing before adequate adhesion is achieved. When the compositions are used as skin barriers, e.g., as a dressing for blisters, some absorption of fluid is desirable, but excessive swelling causes the composition to lose its moisture seal with the skin. Leakage occurs and the barrier must be replaced more often than is desirable. Such problems of conventional hydrocolloid adhesive compositions result in product failure.

A number of attempts have been made to improve the integrity of hydrocolloid adhesive compositions, and the resulting wound dressings and ostomy products. U.S. Pat. No. 4,496,357 describes the incorporation of fumed silica into hydrocolloid compositions to control swelling. U.S. Pat. No. 4,551,490 describes a hydrocolloid adhesive composition of a homogenous blend of mineral oil, one or more polyisobutylenes alone or in combination with an elastomer such as butyl rubber, styrene radial or block copolymers, water-soluble hydrocolloid gums, water-swellable cohesive strengthening agents, and a tackifier. Both the elastomer and water-swellable agents are said to add cohesive strength to the composition, while the styrene radial or block copolymers are said to provide extensibility and recovery from modular strains associated with hydration. See also, U.S. Pat. Nos. 4,204,540, 4,192,785, and 4,166,051.

U.S. Pat. No. 4,952,618 discloses a hydrocolloid adhesive composition formed from a rubbery elastomeric base having hydrocolloid particles, at least some of which are polycationic, dispersed therein. The composition is said to exhibit improved integrity attributable to the polycationic particles contained in the compositions, particularly when combined with anionic hydrocolloid particles, either alone, or further mixed with neutral hydrocolloid particles.

U.S. Pat. Nos. 4,538,603 and 4,728,442 disclose a granular wound packing that is covered with a separate occlusive dressing. In general, the occlusive dressing component can include a variety of hydrocolloid materials in combination with one or more pressure sensitive adhesive elastomers, such as polyisobutylene, and one or more thermoplastic elastomers, such as butyl rubber and styrene copolymers.

Another manner of addressing lack of structural integrity is to provide hydrocolloid adhesive compositions where one or more of the polymeric components are chemically or physically cross-linked. For example, U.S. Pat. No. 4,768,503 provides a adhesive composition of one or more chemically cross-linked hydrophilic polymers in combination with a support matrix of a high molecular weight hydrophobic polymer.

U.S. Pat. Nos. 4,477,325 and 4,738,257 describe incorporating into a hydrocolloid composition a mixture of a copolymer resin of ethylene and vinyl acetate (EVA). After mixing and molding, the composition is subjected to ionizing radiation to form cross-linked polymer networks of the EVA or EVA with another cross-linkable resin. The cross-linked matrix is said to provide controlled swelling.

U.S. Pat. No. 4,231,369 discloses various hydrocolloid materials dispersed within a physically cross-linked gel-like phase. In general, the gel-like phase is comprised of elastomeric materials, such as A-B-A block copolymers, as well as certain ethylene/propylene copolymers, that are said to be physically cross-linked due to phase separation and reformation of the materials after melt processing. The use of elastomeric materials, such as A-B-A block copolymers, is also disclosed by U.S. Pat. Nos. 4,367,732, 4,369,284, 4,867,748 and 5,508,334.

SUMMARY OF THE INVENTION

In general, a wound dressing comprising the composition of the present invention has desirable elastic, adhesive, absorptive and expansion properties as well as a high conformability. The present invention provides a gel-like wound dressing that is comfortable and flexible. The flexibility provides a composition that has the ability to conform to the curvature of body parts while retaining its adhesive properties. The high initial tack at room temperature provides for easy application. While the wound dressing of the present invention is suitable in general for the treatment of wounds that produce exudate, it is particularly suitable for treatment of blisters of the foot, as well as corns and calluses. The embodiments of the invention are also suitable for use as fixation adhesives, especially for breast prostheses, ostomy devices and male incontinence devices, and the like.

The composition comprises about 10 to about 35 weight percent of an elastomer, about 20 to about 60 weight percent of a hydrocolloid, about 25 to about 55 weight percent of a hydrocarbon resin tackifier, about 2 to about 60 weight percent of a non-polar oily extender and no more than about 0.1 weight percent antioxidant, preferably about 0.06 weight percent, of an antioxidant, based on the total weight of the composition.

In other embodiments, the composition comprises about 10 to about 35 weight percent of an elastomer, about 25 to about 55 weight percent of a hydrocarbon resin tackifier, about 2 to about 60 weight percent of a non-polar oily extender and no more than about 0.1 weight percent antioxidant, preferably about 0.06 weight percent, of an antioxidant, based on the total weight of the composition.

The elastomer comprises about 10 to about 35 weight percent of the composition, based on the total weight of the composition. Preferably the elastomer comprises about 11 to about 18 weight percent of the composition, more preferably about 12 to about 16 weight percent of the composition. In one preferred embodiment, the elastomer comprises about 14 weight percent of the composition. In an alternative preferred embodiment, the elastomer comprises about 20 weight percent of the composition. In another preferred embodiment, the elastomer comprises about 30 weight percent of the composition.

Suitable elastomers are thermoplastic elastomers designed for use without vulcanization, such as styrene-olefin-styrene block copolymers. Preferred elastomers are block polymers having either a block of an unsaturated rubber, such as styrene-isoprene-styrene (S-I-S), styrene-butadiene-styrene (S-B-S) or a block of a saturated rubber, such as styrene-ethylene/butylene-styrene (S-E/B-S) or styrene-ethylene/propylene-styrene (S-E/P-S). Preferably, the elastomer is a polymer chosen from the group consisting of Kraton™ D1107 (Shell Chemicals), Kraton™ D1100, Kraton™ D1102, Kraton™ 4000, Kraton™ G1600, Kraton™ G4600 and mixtures thereof. More preferably, the elastomer is a S-I-S polymer such as Kraton™ D1107 (Shell Chemicals).

The hydrocarbon resin tackifier comprises about 20 to about 60 weight percent of the composition, based on the total weight of the composition. Preferably the hydrocarbon resin tackifier comprises about 25 to about 55 weight percent of the composition, more preferably about 30 to about 50 weight percent of the composition. In one preferred embodiment, the hydrocarbon resin tackifier comprises 40 weight percent of the composition.

The hydrocarbon resin tackifier is suitably a hydrogenated tackifier resin that is compatible with styrene. Preferably the hydrocarbon resin tackifier has high initial tack, high clarity, is oxidation resistant and has no adhesive properties when wet. More preferably, the hydrocarbon resin tackifier is a low crystalline hydrogenated tackifier resin. Low crystalline hydrogenated resin tackifiers have been found to impart desirable and useful characteristics to the composition, making a more conformable and flexible wound dressing.

Suitable hydrocarbon resin tackifiers include Wingtack 95 (Goodyear), Wingtack 10 (Goodyear), Wingtack Plus (Goodyear), Wingtack Extra (Goodyear), Wingtack 86 (Goodyear), Foral AX (Hercules, Wilmington, Del.), Foral 85 (Hercules, Wilmington, Del.), Foral 105 (Hercules, Wilmington, Del.), Escorez 1000 (Exxon Chemical), Escorez 5300 (Exxon Chemical), Escorez 40105 (Exxon Chemical). Preferred hydrogenated resin tackifiers are Wingtack 86 and Foral 85. Most preferred is Foral 85.

The composition generally includes a hydrocolloid, but in some specific embodiments the hydrocolloid can be omitted. Compositions formulated without hydrocolloid are especially suitable for applications such as holding breast prostheses or ostomy apparatus in place. Adhesives formulated without hydrocolloid have the advantage that they can be washed and reactivated.

In embodiments containing a hydrocolloid, the hydrocolloid comprises about 20 to about 60 weight percent of the composition, based on the total weight of the composition. Preferably the hydrocolloid comprises about 25 to about 55 weight percent of the composition, more preferably about 30 to about 50 weight percent of the composition. In one preferred embodiment, the hydrocolloid comprises 40 weight percent of the composition.

The hydrocolloid used in the present invention may be synthetically prepared or naturally occurring. Varieties of hydrocolloids within the scope of the present invention include synthetic polymers prepared from single or multiple monomers, naturally occurring hydrophilic polymers or chemically modified naturally occurring hydrophilic polymers.

Non-limiting examples of such hydrocolloids include polyhydroxyalkyl acrylates and methacrylates, polyvinyl lactams, polyvinyl alcohols, polyoxyalkylenes, polyacrylamides, polyacrylic acid, polystyrene sulfonates, natural or synthetically modified polysaccharides, alginates, xanthan gums, guar gums, and cellulosics.

When used in medical applications, the hydrocolloid must also be dermatologically acceptable and non-reactive with the skin of the patient or other components of the composition.

Suitable hydrocolloids include synthetic polymers that may be either linear or crosslinked. Non-limiting examples of synthetic hydrocolloids include polymers prepared from N-vinyl lactams, e.g. N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, and N-vinyl-2-caprolactam.

Other monomers useful to prepare a synthetic hydrocolloid include hydroxyalkyl acrylates and methacrylates, (such as 2-hydroxyethyl acrylate, 2-hydroxyethyl methacrylate, 2-hydroxypropyl acrylate, 2-hydroxypropyl methacrylate, 2,3-dihydroxypropyl methacrylate), acrylic acid, methacrylic acid and a tertiary amino-methacrylimide, (e.g. trimethylamino-methacrylimide), crotonic acid, and pyridine. Additional monomers useful to prepare a synthetic hydrocolloid include water soluble amides, (such as N-(hydroxymethyl)acrylamide and -methacrylamide, N-(3-hydroxpropyl)acrylamide, N-(2-hydroxyethyl)methacrylamide, N-(1,1-dimethyl-3-oxabutyl)acrylamide N-[2-(dimethylamine)ethyl]acrylamide and -methacrylamide, N-[3-(dimethylamino)-2-hydroxylpropyl]methacrylamide, and N-[1,1-dimethyl-2-(hydroxymethyl)-3-oxabutyl]acrylamide); water-soluble hydrazine derivatives, (such as trialkylamine methacrylimide, and dimethyl-(2-hydroxypropyl)amine methacrylimide); monoolefinic sulfonic acids and their salts, (such as sodium ethylene sulfonate, sodium styrene sulfonate and 2-acrylamideo-2-methylpropanesulfonic acid); and the following monomers containing nitrogen in the non-cyclic or cyclic backbone of the monomer: 1-vinyl-imidazole, 1-vinyl-indole, 2-vinyl imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, and 4-acrylyl-morpholine.

Other hydrocolloidal polymers, either naturally occurring or synthetically prepared, are useful in the present invention. These materials include polyvinyl alcohol, polyoxyalkylenes, and such naturally occurring or synthetically modified hydrocolloidal materials as polysaccharides, gums, and modified celluloses.

Representative polysaccharides include starch, glycogen, hemicelluloses, pentosans, gelatin, celluloses, pectin, chitosan, and chitin. Representative gums include Arabic, Locust Bean, Guar, Agar, Carrageenan, Xanthan, Karaya, alginates, tragacanth, Ghatti, and Furcelleran gums. Representative modified celluloses include methyl cellulose, hydroxypropyl methyl cellulose, carboxymethylcellulose, and hydroxypropyl cellulose.

Crosslinking of the linear polymer chains of the hydrocolloid may be desired to improve cohesive properties of the gel dispersed in the pressure sensitive adhesive matrix. When such crosslinking is desired for polymers made from vinyl monomers discussed above, a multi-ethylenically unsaturated compound with the ethylenic groups being vinyl, allyl, or methallyl groups bonded to nitrogen, oxygen or carbon atoms can be used.

Non-limiting examples of crosslinking agents for vinyl containing polymers include divinyl, diallyl, or dimethallyl esters (e.g. ethylene glycol dimethacrylate, divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate); divinyl, diallyl or dimethallyl ethers (e.g. diethyleneglycol divinyl ether, butane diol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether); divinyl, diallyl or dimethallyl amides including bis(N-vinyl lactams), (e.g., 3,3'-ethylene bis(N-vinyl-2-pyrrolidone) and methylene-bis-acrylamide); and divinyl, diallyl and dimethallyl ureas.

Preferable crosslinking agents include ethylene glycol dimethacrylate, methylene-bis-acrylamide, diallyl maleate, and 3,3'-ethylidene bis (N-vinyl-2-pyrrolidone). For n-vinyl lactams, the preferred crosslinking agents are diallyl maleate and 3,3'-ethylidene bis (N-vinyl-2-pyrrolidone). For acrylates and methacrylates, the preferred crosslinking agents are ethylene glycol dimethacrylate and methylene-bis-acrylamide.

Preferred hydrocolloids for the present invention include polysaccharides including starch, glycogen, hemicelluloses, pentosans, gelatin, celluloses, modified celluloses, pectin, chitosan, and chitin. Modified celluloses include methyl cellulose, hydroxypropyl methyl cellulose, carboxymethylcellulose, and hydroxypropyl cellulose. A most preferred hydrocolloid is a water soluble or swellable hydrocolloid chosen from the group consisting of polyvinyl alcohols, powdered pectin, gelatin, methyl cellulose, hydroxypropyl methyl cellulose, carboxymethylcellulose, hydroxypropyl cellulose and mixtures thereof. In one preferred embodiment, the hydrocolloid is carboxymethylcellulose (CMC).

The nonpolar oily extender comprises about 2 to about 60 weight percent of the composition, based on the total weight of the composition. Oils that are polar plasticizers are not suitable for use as the oily extender of the composition of the present invention. Preferably the non-polar oily extender comprises about 2 to about 24 weight percent of the composition, more preferably about 4 to about 10 weight percent of the composition. In one preferred embodiment, the non-polar oily extender comprises 6 weight percent of the composition.

BRIEF DESCRIPTION OF THE DRAWINGS

In the drawings,

FIG. 1 is a graphical representation of the results of a study of water absorption by Compositions A and B; and FIG. 2 is a graphical representation of the results of a study of moisture vapor transfer rate by Compositions A and B.

DETAILED DESCRIPTION OF PREFERRED EMBODIMENTS

It must be noted that, as used in this specification and the appended claims, the singular forms "a", "an" and "the" include plural referents unless the context clearly dictates otherwise. Thus, for example, reference to "a tackifier" includes a mixture of two or more such compounds, reference to "an oily extender" includes mixtures of two or more oily extenders, and the like.

EXAMPLE 1

Formulation of Composition A

Composition A was formulated from the components listed in Table 1.

TABLE 1

| Composition A | |
| --- | --- |
| Component | Weight Percent of Total |
| Elastomer (Kraton-D1107) | 14 |
| Non-polar oily extender (mineral oil) | 6 |
| Hydrocolloid (CMC) | 40 |
| Hydrocarbon resin tackifier (Foral-85) | 40 |

The elastomer, hydrocarbon resin tackifier and non-polar oily extender were heated to 120 degrees Celsius with mixing to form a substantially homogeneous admixture. The hydrocolloid was added to the admixture and mixing was continued until the resulting composition was substantially homogenous. The composition was formed as desired and allowed to cool. Typically the composition was formed into a slab about 0.5 mm thick that was covered on both upper and lower surfaces by release sheets. The properties of Composition A were compared to a commercially available product, Composition B (Compeed®, Coloplast).

EXAMPLE 2

Water Absorption

The water absorption of the compositions was tested as follows. Disks about 2.54 cm (1 inch) in diameter were cut from slabs of Composition A, Composition B or sterilized Composition A using a circular die. The release sheets were removed and the mass in grams was determined by weighing the disk initially ($m_0$) and after 2, 24, 48 and 72 hours immersion in a 0.9% NaCl saline solution. At each time T, the disk was removed from saline, excess fluid was removed using a paper towel, and the disk was weighed to determine $m_T$. The percent water absorption at each time T was calculated as $((m_T-m_0)/m_0) \times 100$. Alternatively, the water absorption was expressed as multiples of the original starting mass of the disk, $((m_T-m_0)/m_0)$.

The water absorption of Composition A, Composition A sterilized by irradiation by beta or gamma rays or Composition B was measured. The results are presented in FIG. 1 and Table 4, below. Composition A showed greater capacity for water absorption than either the commercially available Composition B or sterilized Composition A.

TABLE 2

Water Absorption by Compositions
(Multiples of Initial Mass of Disk)

| | Time (Hours) | | | | | | | |
|---|---|---|---|---|---|---|---|---|
| | 0 | 2 | 4 | 6 | 24 | 48 | 120 | 144 |
| Composition A | 0 | 0.78 | 0.91 | 1.03 | 3.07 | 7.26 | 10.19 | 10.69 |
| Composition B | 0 | 0.34 | 0.39 | 0.61 | 2.43 | 5.10 | 6.76 | 6.93 |
| Sterile Composition A | 0 | 0.51 | 0.82 | 1.02 | 2.18 | 2.02 | | |

EXAMPLE 3
Moisture Vapor Transfer Rate

Disks about 2.54 cm (1 inch) in diameter (an area of about 5cm$^2$) were cut from slabs of Composition A, Composition B or sterilized Composition A using a circular die as described in Example 2. The release sheets were removed and the disks were equilibrated in 0.9% NaCl solution, and then placed in air at room temperature. The disks were weighed at intervals as described in Example 2, above. The results are presented in Table 3, below and in FIG. 2.

Both Composition A and sterilized Composition A demonstrated a good ability to transfer water vapor. In contrast, the commercially available product, Composition B showed little good ability to transfer water vapor.

TABLE 3

Moisture Vapor Transfer Rate
(Water Loss, Grams)

| | Time (Hours) | | | | | | | |
|---|---|---|---|---|---|---|---|---|
| | 0 | 2 | 4 | 6 | 24 | 48 | 120 | 144 |
| Composition A | 202.3 | 202.4 | 202.4 | 202.4 | 202.0 | 201.0 | 197.5 | 196.5 |
| Sterile Composition A | 201.9 | 301.9 | 201.9 | 201.9 | 201.6 | 200.8 | | |
| Composition B | 204.2 | 204.2 | 204.2 | 204.2 | 204.2 | 204.1 | 204 | 203.9 |

These results, and those of Example 2, demonstrate the ability of Composition A to absorb moisture from a oozing or fluid-filled wound, such as a blister, compared to Composition B. These results also show the ability of Composition A to transfer absorbed moisture away from the wound due its relatively high vapor transfer rate.

EXAMPLE 4
Measurement of Cold Flow

Disks about 2.54 cm (1 inch) in diameter were cut from slabs of Composition A, Composition B or sterilized Composition A using a circular die as described in Example 2. The release sheets were removed and the disks were stacked on top of each other, adhering each disk to the next until the height of the stack of disks reached about 0.5 inch. The stack of disks was then placed into a cold flow gauge and the weight was placed on the top of the stack of disks. The initial height of the stack was measured using a micrometer. The height was measured at thirty minute intervals until there was no further change in stack height.

The final percent change in height of the stack of disks after 24 hours was taken as a measure of cold flow. The results were 7.2% for Composition A, and 0.6% for Composition B. The cold flow of Composition A corresponds its greater flexibility relative to Composition B. Methods of maintaining high flexibility and high cohesion of an adhesive dressing by incorporation of a meshwork of polymeric filaments are disclosed in U.S. Pat. No. 5,571,080.

EXAMPLE 5
Skin Peel Test

Strips 2.54 cm (one inch) wide were cut from slabs of wound dressing Composition A or Composition B. A strip of adhesive tape (Scotch™ 3M, Minneapolis, Minn.) to prevent stretching of the samples. The samples were taped to a clamp. The skin of the test volunteer was prepared by washing the underside of the forearm with diluted soap and allowing the skin to dry. The adhesive side of the sample was placed on the prepared skin and the clamp was attached to the hook of the testing device, a Chatillon TCD 200 tensile strength meter. The forearm was placed on the base of the testing device, taking care to keep the end of the sample directly under the clamp. The forearm was kept still while the tensile strength tester was activated to pull the adhesive up at the rate of 12.5 inches per minutes. The peak performance was recorded and any residue left on the skin was noted. The results were: 1.53 lb min /inch for Composition A, and 0.69 lb min /inch for Composition B. The results demonstrate that the composition of the present invention, in an embodiment exemplified by Composition A, has superior adhesiveness compared to the commercially available Composition B.

EXAMPLE 6
Formulation of Composition C

Composition C was formulated from the components listed in Table 4 below.

TABLE 4

| Composition C | |
|---|---|
| Component | Weight Percent of Total |
| Elastomer (Kraton-D1107) | 30 |
| Non-polar oily extender (mineral oil) | 30 |
| Hydrocarbon resin tackifier (Foral-85) | 40 |

The elastomer, hydrocarbon resin tackifier and non-polar oily extender were heated to 120 degrees Celsius with mixing to form a substantially homogeneous admixture. The composition was formed as desired and allowed to cool. Typically the composition was formed into a slab about 0.5 mm thick that was covered on both upper and lower surfaces by release sheets.

In general, Composition C had the advantage that it did not stick to hair, scar tissue or stitches that makes it especially suitable for a post-operative dressing. Composition C did not damage skin when it was removed.

EXAMPLE 7
Formulation of Composition D

Composition D was formulated from the components listed in Table 5 below.

TABLE 5

| Composition D | |
|---|---|
| Component | Weight Percent of Total |
| Elastomer (Kraton-D1107) | 30 |
| Non-polar oily extender (mineral oil) | 30 |
| Hydrocarbon resin tackifier (Escorez 5300) | 40 |

The elastomer, hydrocarbon resin tackifier and non-polar oily extender were heated to 120 degrees Celsius with mixing to form a substantially homogeneous admixture. The composition was formed as desired and allowed to cool. Typically the composition was formed into a slab about 0.5 mm thick that was covered on both upper and lower surfaces by release sheets.

In general, Composition D had the advantage that it did not stick to hair, scar tissue or stitches that makes it especially suitable for a post-operative dressing. Composition D did not damage skin when it was removed. In addition, Composition D exhibited an unexpectedly high moisture vapor transmission rate of 1600 grams water in 24 hours per 100 $cm^2$.

EXAMPLE 8
Formulation of Composition E

Composition E was formulated from the components listed in Table 6 below.

TABLE 6

Composition E

| Component | Weight Percent of Total |
|---|---|
| Elastomer (Kraton-D1107) | 20 |
| Non-polar oily extender (mineral oil) | 20 |
| Hydrocarbon resin tackifier (Foral-85) | 60 |

The elastomer, hydrocarbon resin tackifier and non-polar oily extender were heated to 120 degrees Celsius with mixing to form a substantially homogeneous admixture. The composition was formed as desired and allowed to cool. Typically the composition was formed into a slab about 0.5 mm thick that was covered on both upper and lower surfaces by release sheets.

In general, Composition E was especially suitable as an adhesive for the fixation of breast prostheses. The prostheses could be held in place without a bra or other support, and remained in place during vigorous exercise.

The foregoing is intended to be illustrative of the present invention, but not limiting. Numerous variations and modifications of the present invention may be effected without departing from the true spirit and scope of the invention.

We claim:

1. A flexible and conformable composition suitable for use as a wound dressing consisting essentially of:

about 10 to about 35 weight percent of an elastomer, based on the total weight of the composition;

about 25 to about 55 weight percent of a hydrocarbon resin tackifier, based on the total weight of the composition;

about 2 to about 60 weight percent of an nonpolar oily extender, based on the total weight of the composition;

and no more than about 0.1 weight percent of an antioxidant, based on the total weight of the composition.

2. A flexible and conformable composition suitable for use as a wound dressing consisting essentially of:

about 10 to about 35 weight percent of an elastomer, based on the total weight of the composition;

about 25 to about 55 weight percent of a hydrocarbon resin tackifier, based on the total weight of the composition, wherein the tackifier is selected from the group consisting of Wingtack 95, Wingtack 10, Wingtack Plus, Wingtack Extra, Wingtack 86, Foral AX, Foral 85, Foral 105, Escorez 1000, Escorez 5300, Escorez 40105 and mixtures thereof;

about 2 to about 60 weight percent of an nonpolar oily extender, based on the total weight of the composition;

no more than about 0.1 weight percent of an antioxidant, based on the total weight of the composition; and about 20 and to about 60 weight percent of a hydrocolloid.

3. The composition of claim 1 wherein the elastomer is a styrene-olefin-styrene block co-polymer.

4. The composition of claim 1 wherein the elastomer is about 12 to about 16 weight percent of a styrene-isoprene-styrene block co-polymer, based on the total weight of the composition.

5. The composition of claim 1 wherein the elastomer is about 14 weight percent styrene-isoprene-styrene block co-polymer, based on the total weight of the composition.

6. The composition of claim 2 wherein the elastomer is about 20 weight percent styrene-isoprene-styrene block co-polymer, based on the total weight of the composition.

7. The composition of claim 2 wherein the elastomer is about 30 weight percent styrene-isoprene-styrene block co-polymer, based on the total weight of the composition.

8. The composition of claim 1 wherein the nonpolar oily extender is about 6 weight percent mineral oil, based on the total weight of the composition.

9. The composition of claim 2 wherein the hydrocolloid is carboxymethyl cellulose.

10. The composition of claim 1 wherein the hydrocarbon resin tackifier is a low crystalline structure resin.

11. The composition of claim 1 wherein the hydrocarbon resin tackifier is chosen from the group consisting of Wingtack 95, Wingtack 10, Wingtack Plus, Wingtack Extra, Wingtack 86, Foral AX, Foral 85, Foral 105, Escorez 1000, Escorez 5300, Escorez 40105 and mixtures thereof.

12. The composition of claim 1 wherein the hydrocarbon resin tackifier comprises about 30 to about 60 weight percent Foral 85, based on the total weight of the composition.

13. The composition of claim 1 wherein the hydrocarbon resin tackifier comprises about 40 weight percent Foral 85, based on the total weight of the composition.

14. The composition of claim 1 wherein the hydrocarbon resin tackifier comprises about 60 weight percent Foral 85, based on the total weight of the composition.

15. The composition of claim 1 wherein the hydrocarbon resin tackifier comprises about 40 weight percent Escorez 5300, based on the total weight of the composition.

16. The composition of claim 1 wherein the flexibility of the composition as determined by cold flow is greater than about 1% in 24 hours.

17. The composition of claim 2 wherein the composition absorbs water more than about 2.5 times its mass in the first 24 hours of contact with the wound.

18. The composition of claim 1 wherein the composition has a moisture vapor transmission rate of about 1600 grams of water in 24 hours per 100 $cm^2$.

19. The composition of claim 2 wherein the hydrocarbon resin tackifier comprises about 40 weight percent Foral 85, based on the total weight of the composition.

* * * * *